(12) United States Patent
Nakamura et al.

(10) Patent No.: US 11,224,581 B2
(45) Date of Patent: Jan. 18, 2022

(54) COMPOSITION FOR PROMOTING KETONE BODY PRODUCTION

(71) Applicant: Meiji Co., Ltd., Tokyo (JP)

(72) Inventors: Kentaro Nakamura, Odawara (JP); Kinya Ashida, Odawara (JP); Akina Sasayama, Odawara (JP); Yuri Saito, Odawara (JP)

(73) Assignee: Meiji Co., Ltd.

( * ) Notice: Subject to any disclaimer, the term of this patent is extended or adjusted under 35 U.S.C. 154(b) by 335 days.

(21) Appl. No.: 16/326,260

(22) PCT Filed: Aug. 18, 2017

(86) PCT No.: PCT/JP2017/029587
§ 371 (c)(1),
(2) Date: Feb. 18, 2019

(87) PCT Pub. No.: WO2018/034330
PCT Pub. Date: Feb. 22, 2018

(65) Prior Publication Data
US 2019/0183828 A1 Jun. 20, 2019

(30) Foreign Application Priority Data

Aug. 19, 2016 (JP) .............................. JP2016-161267

(51) Int. Cl.
| | |
|---|---|
| A61K 31/195 | (2006.01) |
| A61K 31/16 | (2006.01) |
| A61K 31/198 | (2006.01) |
| A61K 31/185 | (2006.01) |
| A23L 33/175 | (2016.01) |
| A61P 25/08 | (2006.01) |
| A61K 31/23 | (2006.01) |
| A61P 35/00 | (2006.01) |
| A61P 25/16 | (2006.01) |
| A61P 25/06 | (2006.01) |
| A61P 43/00 | (2006.01) |
| A61K 31/20 | (2006.01) |
| A61P 3/04 | (2006.01) |
| A61P 9/10 | (2006.01) |
| A61P 25/00 | (2006.01) |
| A61P 25/28 | (2006.01) |
| A61P 9/04 | (2006.01) |
| A61P 3/10 | (2006.01) |
| A61P 25/24 | (2006.01) |
| A23L 33/12 | (2016.01) |
| A61P 3/02 | (2006.01) |
| A61K 31/225 | (2006.01) |

(52) U.S. Cl.
CPC ............ *A61K 31/198* (2013.01); *A23L 33/12* (2016.08); *A23L 33/175* (2016.08); *A61K 31/185* (2013.01); *A61K 31/20* (2013.01); *A61K 31/225* (2013.01); *A61K 31/23* (2013.01); *A61P 3/02* (2018.01); *A61P 3/04* (2018.01); *A61P 3/10* (2018.01); *A61P 9/04* (2018.01); *A61P 9/10* (2018.01); *A61P 25/00* (2018.01); *A61P 25/06* (2018.01); *A61P 25/08* (2018.01); *A61P 25/16* (2018.01); *A61P 25/24* (2018.01); *A61P 25/28* (2018.01); *A61P 35/00* (2018.01); *A61P 43/00* (2018.01); *A23V 2002/00* (2013.01)

(58) Field of Classification Search
CPC .............................. A61K 31/195; A61K 31/16
USPC .................... 514/561, 562, 563, 564, 578
See application file for complete search history.

(56) References Cited

U.S. PATENT DOCUMENTS

| | | | |
|---|---|---|---|
| 8,124,589 B2 | 2/2012 | Henderson | |
| 9,138,420 B2 | 9/2015 | D'Agostino et al. | |
| 2009/0054351 A1 | 2/2009 | Matuschka-Greiffenclau | |
| 2018/0169052 A1 | 6/2018 | Kunugi et al. | |

FOREIGN PATENT DOCUMENTS

| | | | | |
|---|---|---|---|---|
| JP | 6287138 A | 10/1994 | | |
| JP | 9121809 A | 5/1997 | | |
| JP | 2008255033 A | 10/2008 | | |
| JP | 2009532496 A | 9/2009 | | |
| JP | 2009261335 A | 11/2009 | | |
| JP | 2011136948 A | 7/2011 | | |
| JP | 2013189437 A | 9/2013 | | |
| JP | 2016210720 A | 12/2016 | | |
| JP | 2016161267 | 3/2021 | | |
| WO | 2007115282 A2 | 10/2007 | | |
| WO | WO-2012085954 A1 * | 6/2012 | ............. | A61K 45/06 |

(Continued)

OTHER PUBLICATIONS

Abe et al., "Medium-Chain Triglycerides in Combination with Leucine and Vitamin D Benefit Cognition in Frail Elderly Adults: A Randomized Controlled Trial", J Nutr Sci Vitaminol, 2017, pp. 133-140, vol. 63.

(Continued)

*Primary Examiner* — Raymond J Henley, III
(74) *Attorney, Agent, or Firm* — The Webb Law Firm

(57) ABSTRACT

An object of the present invention is to provide a novel composition for promoting ketone body production. The present invention provides a composition for use in promoting ketone body production, comprising one or more amino acid(s) selected from the group consisting of citrulline, leucine, cysteine, taurine, glutamine and aspartic acid. The composition according to the present invention may further comprise either or both of a medium-chain fatty acid and a medium-chain fatty acid ester.

7 Claims, 5 Drawing Sheets

(56) References Cited

FOREIGN PATENT DOCUMENTS

| WO | 2014153416 A1 | 9/2014 |
|----|---------------|--------|
| WO | 2016013617 A1 | 1/2016 |

OTHER PUBLICATIONS

Baranano et al., "The Ketogenic Diet: Uses in Epilepsy and Other Neurologic Illnesses", Current Treatment Options in Neurology, 2008, pp. 410-419, vol. 10.

Gasior et al., "Neuroprotective and disease-modifying effects of the ketogenic diet", Behav Pharmacol., Sep. 2006, pp. 1-15, vol. 17, No. 5-6.

Henderson et al., "Study of the ketogenic agent AC-1202 in mild to moderate Alzheimer's disease: a randomized, double-blind, placebo-controlled, multicenter trial", Nutrition & Metabolism, 2009, vol. 6, No. 31.

Nishizono et al., "Relationship Between Decreased Accumulation and Secretion of Cholesterol Ester and Fatty Acid Oxidation in the Liver of Taurine Diet-Fed Rats", Japanese Journal of Taurine Research, 2015, 4 pgs., vol. 1.

Pi-Sunyer et al., "Insulin and Ketone Responses to Ingestion of Medium and Long-chain Triglycerides in Man", Diabetes, 1969, pp. 96-100, vol. 18, No. 2.

Yeh et al., "Ketone Body Synthesis from Leucine by Adipose Tissue from Different Sites in the Rat", Archives of Biochemistry and Biophysics, 1984, pp. 10-18, vol. 233, No. 1.

Joffin et al., "Citrulline reduces glyceroneogenesis and induces fatty acid release in visceral adipose tissue from overweight rats", Molecular Nutrition and Food Research, 2014, pp. 2320-2330, vol. 58, No. 12.

Kaore et al., "Citrulline: pharmacological perspectives and its role as an emerging biomarker in future", Fundamental & Clinical Pharmacology, 2013, pp. 35-50, vol. 27, No. 1.

Liu, "Medium-chain triglyceride (MCT) ketogenic therapy", Epilepsia, 2008, pp. 33-36, vol. 49, No. 8.

"Ketogenic amino acid", Wikipedia, retrieved from https://web.archive.org/web/20160311070633/https://en.wikipedia.org/wiki/ketogenic_amino_acid.

Xu et al., "Amino Acid Metabolism: Individual Amino Acid Metabolic Pathways", Medical Biochemistry, 1st Edition, Oct. 10, 1998, pp. 359.

* cited by examiner

[FIG. 3]
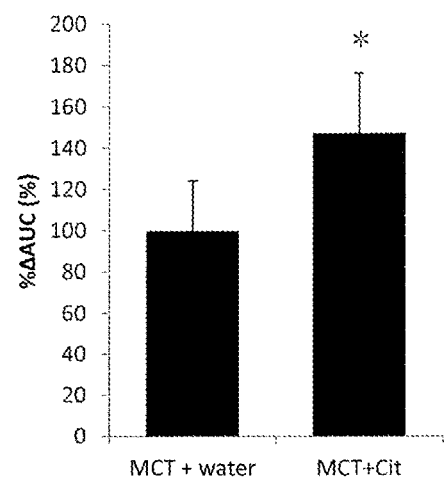
[FIG. 4]
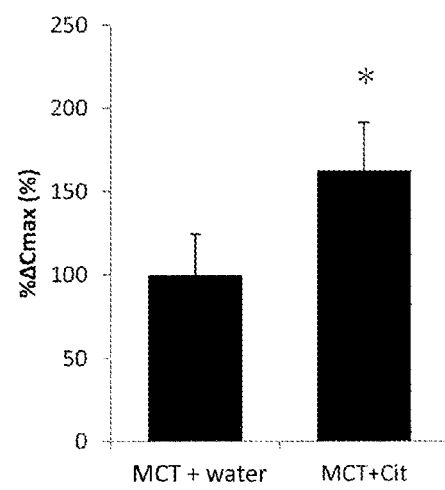

[FIG. 5]
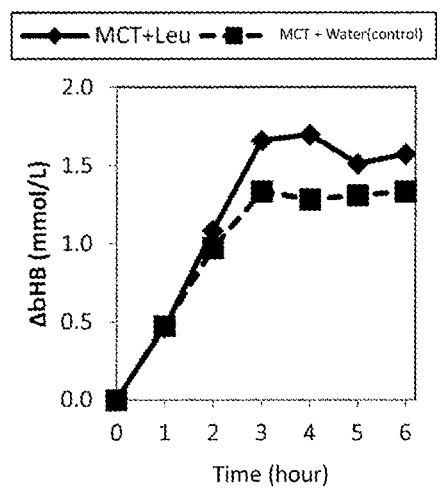
[FIG. 6]
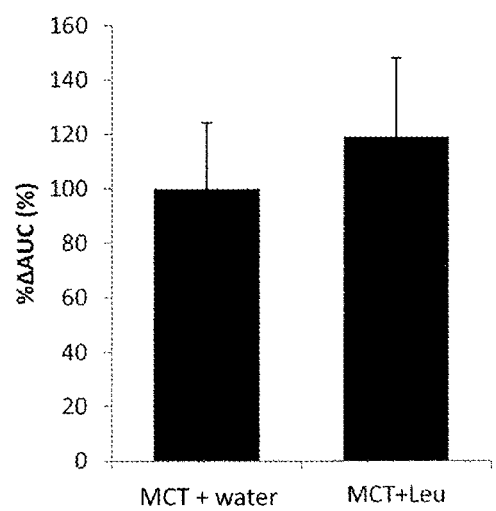

[FIG. 7]
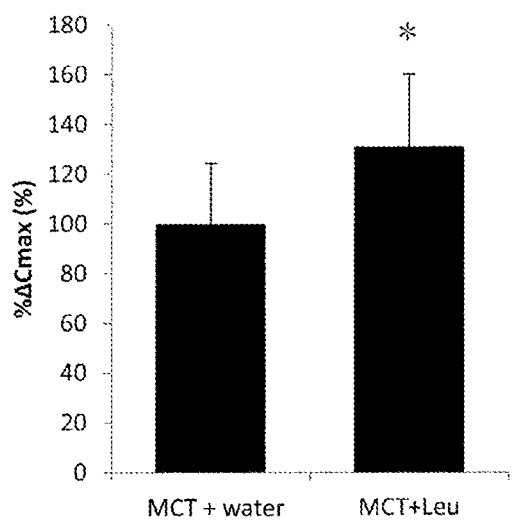
[FIG. 8]
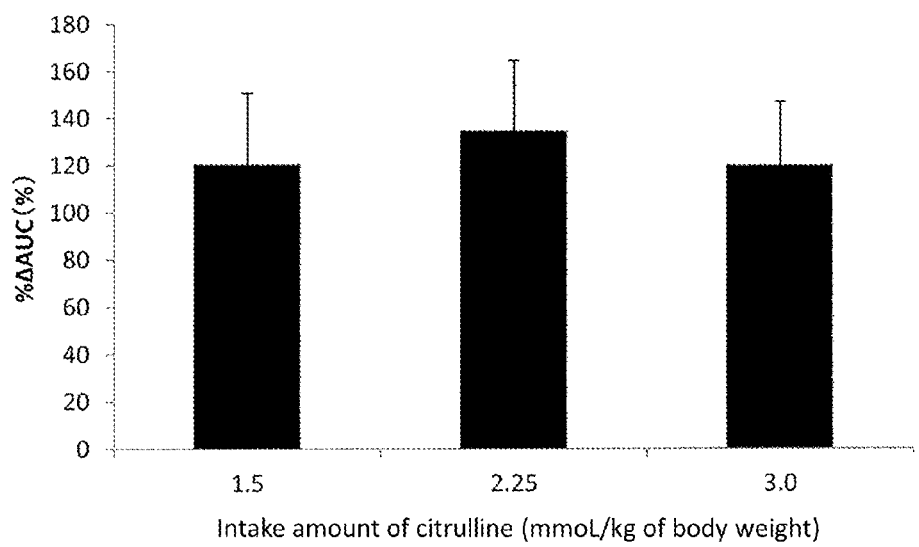

[FIG. 9]
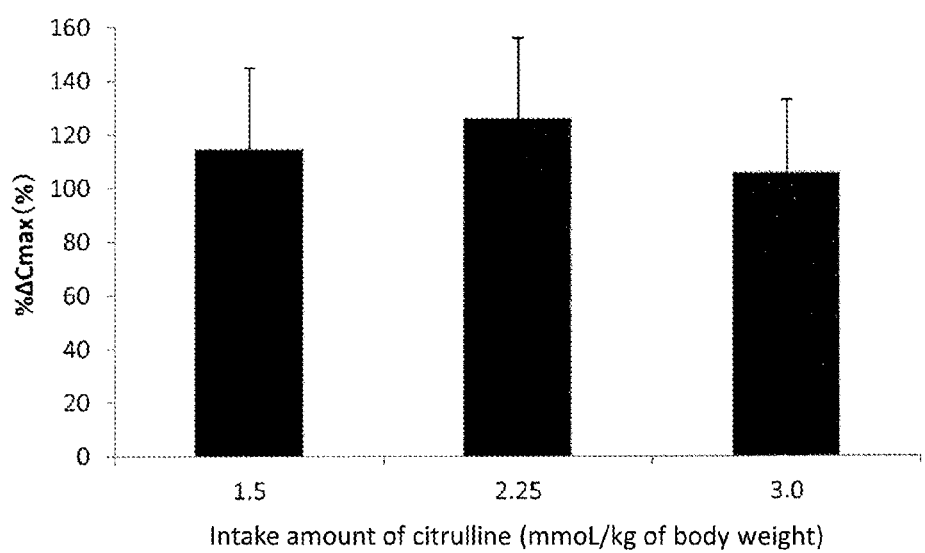

COMPOSITION FOR PROMOTING KETONE BODY PRODUCTION

CROSS-REFERENCE TO RELATED APPLICATION

This application is the United States national phase of International Application No. PCT/JP2017/029587 filed Aug. 18, 2017, and enjoys the benefit of priority from the prior Japanese Patent Application No. 2016-161267 filed on Aug. 19, 2016, the entire disclosures of which are incorporated herein by reference.

TECHNICAL FIELD

The present invention relates to a composition for use in promoting ketone body production.

BACKGROUND ART

The "ketone body" is a generic term for acetoacetic acid, β-hydroxybutyric acid and acetone. Normally, fatty acids are β-oxidized in the liver to form acetyl CoA, which is completely oxidized in the TCA cycle. On the other hand, lack of carbohydrates necessary for the TCA cycle causes insufficient rotation of the TCA cycle so that acetyl CoA is accumulated and converted into acetoacetic acid via acetoacetyl CoA. Acetoacetic acid is decarbonized into acetone and enzymatically reduced into β-hydroxybutyric acid. Due to the reduction in glucose in the tissue caused by diabetes and the lack of carbohydrates caused by fasting, the ketone body production in the liver increases, and the ketone bodies are utilized as an energy source. Similarly to glucose and the like, the ketone bodies are utilized as an energy source in many tissues. Especially, the brain utilizes only glucose and ketone bodies as energy sources. When glucose is depleted, the ketone bodies serve as the only energy source and thus play an important role.

It has become clear that ketogenic diet, which is a dietary regimen involving production of a lot of ketone bodies in a living body, is useful for prevention, treatment and the like of various diseases. Ketone diet is a high-fat low-carbohydrate diet in which ketone body production is promoted by extreme decrease in carbohydrate intake and intake of a lot of fat. Ketogenic diet is known to be useful for the treatment of intractable epilepsy and GLUT1 deficiency and the suppression of seizures of intractable epilepsy, and, more recently, has been reported to be useful for the prevention and treatment of neurodegenerative diseases such as Alzheimer's disease (Non-Patent Documents 1 and 2).

In general, fatty acids are classified into long-chain fatty acids, medium-chain fatty acids, and short-chain fatty acids depending on the length of the carbon chain. Medium-chain fatty acids are considered to efficiently produce ketone bodies as compared with long-chain fatty acids due to the difference in pathway of absorption/metabolism, and, in humans and animals, medium-chain fatty acid oil and fat is known to increase the concentration of ketone bodies in the blood as compared with long-chain fatty acid oil and fat (Non-Patent Document 3). However, side effects such as diarrhea and vomiting are sometimes caused by intake of medium-chain fatty acid oil and fat, which makes practical intake of the medium-chain fatty acid oil and fat difficult (Non-Patent Document 4).

REFERENCE LIST

Non-Patent Documents

Non-Patent Document 1: Maciej Gasior, et al., Behav Pharmacol., 2006; 17(5-6): p. 431-439
Non-Patent Document 2: Kristin W. et al., Curr Treat Options Neurol. 2008; 10(6): p. 410-416
Non-Patent Document 3: Pi-Sunyer F X, et al., Diabetes., 1969; 18(2): p. 96-100
Non-Patent Document 4: Henderson et al., Nutr Metalab (Lond). 2009; 6: 31 doi: 10.1186/1743-7075-6-31

SUMMARY OF THE INVENTION

The present inventors have found that the ketone body production from a medium-chain fatty acid and a medium-chain fatty acid ester in a living body can be further promoted upon intake of a specific amino acid. The present invention is based on this finding.

Namely, an object of the present invention is to provide a novel composition for promoting ketone body production and a novel agent for promoting ketone body production.

The present invention provides the following inventions.
[1] A composition for use in promoting ketone body production and an agent for promoting ketone body production (hereinafter referred to as the "composition and agent according to the present invention" in some cases), comprising, as an active ingredient, one or more amino acid(s) selected from the group consisting of citrulline, leucine, cysteine, taurine, glutamine and aspartic acid.
[2] The composition and agent according to [1], which further comprise either or both of a medium-chain fatty acid and a medium-chain fatty acid ester.
[3] The composition and agent according to [1] or [2], wherein the medium-chain fatty acid ester is a medium-chain triglyceride.
[4] The composition and agent according to [2] or [3], wherein the molar ratio [(A)/(B)] of the amino acid(s) (A) to the medium-chain fatty acid and medium-chain fatty acid ester (B) ranges from 0.1 to 0.5.
[5] The composition and agent according to any one of [1] to [4], which are each a food composition.
[6] The composition and agent according to any one of [1] to [5], which are for use in treating, preventing or improving a disease or symptom that is to be effectively treated, prevented or improved by promoting ketone body production.
[7] The composition and agent according to [6], wherein the disease and symptom are one or more selected from the group consisting of childhood epilepsy, intractable epilepsy, glucose transporter 1 (GLUT1) deficiency, pyruvate dehydrogenase complex disorder, Alzheimer's disease, neurodegenerative disease, mild cognitive impairment, Parkinson's disease, traumatic brain injury, cancer, depression, autism, migraine, amyotrophic lateral sclerosis, narcolepsy, diabetes, heart failure, myocardial infarction, angina pectoris, and obesity.
[8] A method for promoting ketone body production and a method for treating, preventing or improving a disease or symptom that is to be effectively treated, prevented or improved by promoting ketone body production, the methods comprising feeding or administering one or more amino acid(s) selected from the group consisting of citrulline, leucine, cysteine, taurine, glutamine and aspartic acid to a mammal.

[9] The method for promoting ketone body production and the treating, preventing or improving method according to [8], which comprise feeding or administering either or both of a medium-chain fatty acid and a medium-chain fatty acid ester in addition to the amino acid(s).

[10] Use of one or more amino acid(s) selected from the group consisting of citrulline, leucine, cysteine, taurine, glutamine and aspartic acid, for the manufacture of an agent for promoting ketone body production or an agent for treating, preventing or improving a disease or symptom that is to be effectively treated, prevented or improved by promoting ketone body production.

[11] Use of a combination of one or more amino acid(s) selected from the group consisting of citrulline, leucine, cysteine, taurine, glutamine and aspartic acid and either or both of a medium-chain fatty acid and a medium-chain fatty acid ester, for the manufacture of an agent for promoting ketone body production or an agent for treating, preventing or improving a disease or symptom that is to be effectively treated, prevented or improved by promoting ketone body production.

[12] One or more amino acid(s) selected from the group consisting of citrulline, leucine, cysteine, taurine, glutamine and aspartic acid, for use in the promotion of ketone body production or for use in the treatment, prevention or improvement of a disease or symptom that is to be effectively treated, prevented or improved by promoting ketone body production.

[13] A combination of one or more amino acid(s) selected from the group consisting of citrulline, leucine, cysteine, taurine, glutamine and aspartic acid and either or both of a medium-chain fatty acid and a medium-chain fatty acid ester, for use in the promotion of ketone body production or for use in the treatment, prevention or improvement of a disease or symptom that is to be effectively treated, prevented or improved by promoting ketone body production.

[14] Use of one or more amino acid(s) selected from the group consisting of citrulline, leucine, cysteine, taurine, glutamine and aspartic acid, as an agent for promoting ketone body production or as an agent for treating, preventing or improving a disease or symptom that is to be effectively treated, prevented or improved by promoting ketone body production.

[15] Use of a combination of one or more amino acid(s) selected from the group consisting of citrulline, leucine, cysteine, taurine, glutamine and aspartic acid and either or both of a medium-chain fatty acid and a medium-chain fatty acid ester, as an agent for promoting ketone body production or as an agent for treating, preventing or improving a disease or symptom that is to be effectively treated or improved by promoting ketone body production.

The composition and agent according to the present invention can be used to produce a sufficient amount of ketone bodies in a living body while reducing the intake amount of a medium-chain fatty acid and a medium-chain fatty acid ester for the purpose of promoting ketone body production from the medium-chain fatty acid and medium-chain fatty acid ester in a living body. Therefore, the composition and agent according to the present invention are advantageous in that they can promote the ketone body production in a living body while reducing side effects. Further, the composition and agent according to the present invention are advantageous in that they comprise, as an active ingredient, an amino acid which has been established to have safety, and thus can be fed safely over a long term and also can realize the continuation of treatment applied to persons who are addressing the prevention and treatment of various diseases and the improvement in their QOL.

BRIEF DESCRIPTION OF THE DRAWINGS

FIG. 3 shows the area under the blood concentration-curve (ΔAUC) of β-hydroxybutyric acid (% relative value for the experimental group when the value for the control group is assumed to be 100) until 6 hours after simultaneous feeding of citrulline (Cit) and medium-chain fatty acid oil and fat (MCT); t-test, *: p<0.05 vs control group.

FIG. 4 shows the maximum blood concentration (ΔCmax) of β-hydroxybutyric acid (% relative value for the experimental group when the value for the control group is assumed to be 100) until 6 hours after simultaneous feeding of citrulline (Cit) and medium-chain fatty acid oil and fat (MCT).; t-test, *: p<0.05 vs control group.

FIG. 5 is a graph showing the transition of the amount of change (ΔbHB) in concentration of β-hydroxybutyric acid (bHB) in the blood until 6 hours after simultaneous feeding of leucine (Leu) and medium-chain fatty acid oil and fat (MCT) for the experimental group and the control group.

FIG. 6 shows the area under the blood concentration-curve (ΔAUC) of β-hydroxybutyric acid (% relative value for the experimental group when the value for the control group is assumed to be 100) until 6 hours after simultaneous feeding of leucine (Leu) and medium-chain fatty acid oil and fat (MCT).

FIG. 7 shows the maximum blood concentration (ΔCmax) of β-hydroxybutyric acid (% relative value for the experimental group when the value for the control group is assumed to be 100) until 6 hours after simultaneous feeding of leucine (Leu) and medium-chain fatty acid oil and fat (MCT); t-test, *: p<0.05 vs control group.

FIG. 8 shows the area under the blood concentration-curve (ΔAUC) of β-hydroxybutyric acid (% relative value for the experimental group when the value for the control group is assumed to be 100) until 6 hours after simultaneous feeding of citrulline (Cit) with varying intake amount and medium-chain fatty acid oil and fat (MCT) in a constant amount.

FIG. 9 shows the maximum blood concentration (ΔCmax) of β-hydroxybutyric acid (% relative value for the experimental group when the value for the control group is assumed to be 100) until 6 hours after simultaneous feeding of citrulline (Cit) with varying intake amount and medium-chain fatty acid oil and fat (MCT) in a constant amount.

DETAILED DESCRIPTION OF THE INVENTION

Figure 1A:
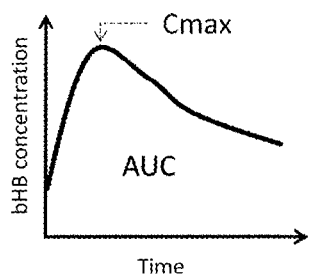
FIG. 1A is a reference view showing the maximum blood concentration (Cmax) and area under the blood concentration-curve (AUC) of the β-hydroxybutyric acid concentration (bHB (mmol/L)) until the elapse of a predetermined time from an initial value (0 hours). The blood β-hydroxybutyric acid concentration at the initial value (0 hours) represents the concentration of β-hydroxybutyric acid originally present in the blood before feeding of a test substance.

The composition for use in promoting ketone body production according to the present invention is characterized in that it comprises, as an active ingredient, one or more amino acid(s) (at least one amino acid) (hereinafter referred to as the "amino acid of the present invention" in some cases) selected from the group consisting of citrulline (Cit), leucine (Leu), cysteine (Cys), taurine (Tau), glutamine (Gln) and aspartic acid (Asp).

The amino acid of the present invention may be a free body or a hydrate, and may also be a salt. Examples of the salt of the amino acid include acid addition salts (for example, organic acid salts such as acetic acid salts, tartaric acid salts and fatty acid salts; and inorganic acid salts such as hydrochloric acid salts, hydrobromic acid salts, nitric acid salts, sulfuric acid salts and perchloric acid salts), salts with organic bases (for example, organic amine addition salts such as morpholine), and salts with inorganic bases (for example, metal salts such as potassium salt, sodium salt and zinc salt, and ammonium salts). The amino acid of the present invention may be any of L-bodies, D-bodies and DL-bodies thereof. The use of L-bodies is preferred.

The amino acid of the present invention can be obtained, for example, from materials and foods containing a large amount of the amino acid, by squeezing, concentration, purification, crystallization, extraction with various solvents, or the like. As such various solvents, water and commonly-used solvents such as alcohols, hydrocarbons, organic acids, organic bases, inorganic acids, inorganic bases and supercritical fluids can be used alone or in combination. Microbially-produced solvents, chemically-synthesized solvents or commercially-available solvents may also be used.

Among the amino acids of the present invention, citrulline was found from watermelons. Due to its presence in a variety of living organisms, citrulline extracted (including rough extraction) or purified or roughly purified from these living organisms or processed products thereof can be typically used as the active ingredient of the present invention. Also, citrulline prepared by a chemical synthesis method may be used as a part or the whole of citrulline. Since citrulline is commercially available, commercially-available products may be used.

The amino acid of the present invention has the action of promoting ketone body production in a living body, as will be illustrated in the Examples below. Thus, the amino acid of the present invention can be used as the active ingredient of the composition for use in promoting ketone body production and the agent for promoting ketone body production, and can also be used as the active ingredient in the method for promoting ketone body production.

Here, the phrases "promoting ketone body production" and "promotion of ketone body production" mean that the ketone body production in a living body is promoted, and the degree of promotion of ketone body production can be evaluated, for example, by using the blood β-hydroxybutyric acid concentration (mmol/L) as an index of the ketone body in the blood (see the section "Evaluation of ketone body production" in the Examples). In particular, the degree of promotion of ketone body production can be evaluated by measuring the blood β-hydroxybutyric acid concentrations both when either or both of a medium-chain fatty acid and a medium-chain fatty acid ester is/are fed alone (single feeding) and when either or both of a medium-chain fatty acid and a medium-chain fatty acid ester is/are fed in combination with the amino acid (combined feeding), and comparing the single feeding and the combined feeding in terms of the maximum value (ΔCmax) of the amount of change in blood β-hydroxybutyric acid concentration and the area under the curve (ΔAUC). When both ΔCmax and ΔAUC in the combined feeding take higher values than those in the single feeding, it can be determined that ketone body production has been promoted.

Here, the term "medium-chain fatty acid" refers to saturated fatty acids having 6 to 12 carbon atoms. Examples of the medium-chain fatty acid include lauric acid, caprylic acid, capric acid, caproic acid, heptylic acid, and pelargonic acid. The term "medium-chain fatty acid ester" means esters of medium-chain fatty acids, and examples thereof include medium-chain triglycerides (MCTs) having a structure with an ester bond between a medium-chain fatty acid and glycerin (for example, caprylic triglyceride and capric triglyceride). The "medium-chain triglyceride" used herein is sometimes referred to as "medium-chain fatty acid oil and fat."

Since medium-chain fatty acids and medium-chain fatty acid esters are present in vegetables such as coconut and palm fruit and dairy products such as cow milk, medium-chain fatty acids and medium-chain fatty acid esters extracted (including rough extraction) or purified or roughly purified therefrom can be used in the present invention. Or, products obtained by a chemical synthesis method and commercially-available products may be used as a part or the whole of the medium-chain fatty acid and medium-chain fatty acid ester.

The content of the amino acid of the present invention in the composition and agent according to the present invention is not particularly limited as long as the ketone body production promoting effect due to the amino acid of the present invention can be obtained. However, from the viewpoint of efficient feeding and administration of the amino acid of the present invention, the content of the amino acid in the composition and agent can be set, for example, to 1 to 20% by mass per solid content of the composition and agent, and is preferably 2 to 15% by mass, more preferably 3 to 12% by mass. When two or more amino acids of the present invention are blended in the composition and agent according to the present invention, the content (%) of the amino acid defined above is the total content of the two or more amino acids.

The amino acid of the present invention promotes the ketone body production from a medium-chain fatty acid or an ester thereof in a living body through oral feeding, as will be illustrated in the Examples below. Therefore, the composition and agent according to the present invention are preferably fed or administered together with either or both of the medium-chain fatty acid and the medium-chain fatty acid ester.

The composition and agent according to the present invention can be fed simultaneously with a normal food or before or after feeding thereof, or between meals. Examples of the food to be fed together with the composition and agent according to the present invention include foods containing an ingredient which serves as a source of ketone body production in a living body (for example, a fatty acid and a fatty acid ester). From the viewpoint of better exertion of the ketone body production promoting effect due to the amino acid of the present invention, a food containing either or both of a medium-chain fatty acid and a medium-chain fatty acid ester is preferred.

Examples of the food containing either or both of a medium-chain fatty acid and a medium-chain fatty acid ester include, but are not limited to, Ketonformula (manufactured by Meiji Co. Ltd.), Macton oil (manufactured by Kissei Pharmaceutical Co., Ltd.), MCT powder (manufactured by The Nissin Oillio Group, Ltd.), coconut oil and foods added with these foods.

When the composition and agent according to the present invention are fed or administered together with either or both of a medium-chain fatty acid and a medium-chain fatty acid ester, the composition and agent are fed so that the molar ratio [(A)/(B)] of the amino acid (A) of the present invention to the medium-chain fatty acid and medium-chain fatty acid ester (B) falls within the range of preferably 0.1 to 0.5, more preferably 0.15 to 0.3, from the viewpoint of promoting the ketone body production in a living body. Also when the composition and agent according to the present invention are fed together with a food containing either or both of a medium-chain fatty acid and a medium-chain fatty acid ester, the amount of the medium-chain fatty acid and medium-chain fatty acid ester contained in the food can be determined according to the above ratio. Additionally, when two or more amino acids of the present invention are blended in the composition and agent according to the present invention, the content (mole) of the amino acid based on which the molar ratio is calculated is the total content of the two or more amino acids. When either of a medium-chain fatty acid and a medium-chain fatty acid ester is fed or administered, the above molar ratio is the molar ratio of the amino acid (A) to either of a medium-chain fatty acid and a medium-chain fatty acid ester, of course.

According to a preferred embodiment of the present invention, there is provided a composition for use in promoting ketone body production and an agent for promoting ketone body production, further comprising either or both of a medium-chain fatty acid and a medium-chain fatty acid ester in addition to the amino acid of the present invention. The composition and agent make it possible to provide the amino acid of the present invention having the action of promoting ketone body production in a living body and either or both of a medium-chain fatty acid and a medium-chain fatty acid ester which serve(s) as a source of ketone body production together. Therefore, the composition and agent are advantageous in that ketone bodies can be efficiently produced in a living body.

The molar ratio [(A)/(B)] of the amino acid (A) of the present invention to the medium-chain fatty acid and medium-chain fatty acid ester (B) in the composition and agent according to the present invention ranges preferably from 0.1 to 0.5, more preferably from 0.15 to 0.3. Additionally, when two or more amino acids of the present invention are blended in the composition and agent according to the present invention, the content (mole) of the amino acid based on which the molar ratio is calculated is the total content of the two or more amino acids. When either of a medium-chain fatty acid and a medium-chain fatty acid ester is contained in the composition and agent according to the present invention, the above molar ratio is the molar ratio of the amino acid (A) to either of a medium-chain fatty acid and a medium-chain fatty acid ester, of course.

The method for promoting ketone body production according to the present invention can be carried out by feeding or administering an effective amount of the amino acid of the present invention to a human or non-human animal. In the method for promoting ketone body production according to the present invention, as with the composition and agent according to the present invention, it is preferable to feed or administer the amino acid of the present invention together with either or both of a medium-chain fatty acid and a medium-chain fatty acid ester. From the viewpoint of efficient ketone body production in a living body, it is more preferable to feed or administer a composition comprising the amino acid of the present invention and either or both of a medium-chain fatty acid and a medium-chain fatty acid ester.

The use of the amino acid of the present invention is intended to include both of therapeutic use and non-therapeutic use among uses thereof in a human and a non-human animal. Here, the term "non-therapeutic" means exclusion of activities of performing an operation, treatment or diagnosis on a human (i.e., medical activities to a human), and specifically means exclusion of a method of performing an operation, treatment or diagnosis on a human by a doctor or a person who receives doctor's instructions.

The amino acid of the present invention can promote the ketone body production from the medium-chain fatty acid and medium-chain fatty acid ester in a living body, as will be illustrated in the Examples below. It has been reported so far that childhood epilepsy and intractable epilepsy can be prevented or treated by promoting ketone body production in a living body (Non-Patent Documents 1 and 2). It has also been reported that the use of glucose is reduced in the brains of patients suffering from Alzheimer's disease and mild cognitive impairment, thereby reducing the brain function and the cognitive function, and that Alzheimer's disease and mild cognitive impairment can be prevented or treated by ketone body production (Non-Patent Documents 1 and 2). Thus, the composition and agent according to the present invention can be used in the treatment, prevention or improvement of a disease and a symptom that are to be effectively treated, prevented or improved by promoting ketone body production. In other words, the amino acid of the present invention can be used as the active ingredient of the composition for use in the treatment, prevention and improvement of the above diseases and symptoms and can also be used as the active ingredient of the agents for treating, preventing and improving the above diseases and symptoms. The amino acid of the present invention can also be used in the methods for treating, preventing and improving the above diseases and symptoms, and, specifically, an effective amount thereof can be administered to a human or non-human animal.

Examples of the diseases and symptoms that are to be effectively treated, prevented or improved by promoting ketone body production include childhood epilepsy, intractable epilepsy, glucose transporter 1 (GLUT1) deficiency, pyruvate dehydrogenase complex disorder, Alzheimer's disease, neurodegenerative disease such as muscular dystrophy, mild cognitive impairment, Parkinson's disease, traumatic brain injury, cancer, depression, autism, migraine, amyotrophic lateral sclerosis, narcolepsy, diabetes, heart failure, myocardial infarction, angina pectoris, and obesity (Non-Patent Documents 1 and 2 and Paoli A. et al., Eur J Clin Nutr. 2013; 67: p. 789-796).

The composition and agent for use in promoting ketone body production according to the present invention can be provided in the form of pharmaceutical products, quasi-drugs, foods, feeds, and the like, and can be carried out according to the following description. Also, the method for promoting ketone body production according to the present invention and the treating, preventing and improving methods according to the present invention can be carried out according to the following description.

The composition and agent according to the present invention can be orally fed or orally administered, as pharmaceutical products or supplements, to a human and a non-human animal. Examples of oral agents include tablets (including sugar-coated tablets), pills, capsules, granules, powdered drugs and syrups. These formulations can be formulated by using a pharmaceutically acceptable carrier by a technique commonly used in the art. Examples of the pharmaceutically acceptable carrier include excipients, binders, disintegrants, lubricants, odor improving agents, solubilizers, suspensions, coating agents, perfumes, buffers, thickeners, colorants, stabilizers and emulsifiers. Further, an appropriate amount of a vitamin, a mineral, an organic acid, a saccharide, a peptide or the like may be added to the composition and agent according to the present invention.

In the present invention, administration to a human and a non-human animal other than oral administration, including tube administration, nasal tube administration, drip infusion and suppositories, can also be adopted according to the form of the composition and agent according to the present invention. For example, the composition and agent according to the present invention are each prepared in the form of a viscous liquid composition or a semi-solid composition, and thus can be administered also to humans and non-human animals having deteriorated chewing and swallowing functions so that oral feeding or oral administration cannot be adopted. By feeding or administering the composition and agent according to the present invention in a way other than oral feeding, ketone body production can be promoted in humans and non-human animals even though their chewing and swallowing functions are deteriorated, for example, with aging. In addition, the treatment, prevention and improvement of diseases that are to be effectively treated, prevented or improved by promoting ketone body production and symptoms related to the diseases can be expected.

The composition and agent according to the present invention are prepared by using, as raw materials, ingredients contained in daily food materials, such as an amino acid and a medium-chain fatty acid and a medium-chain fatty acid ester, while having the action of promoting ketone body production in a living body, and thus can be provided as foods fed daily, foods fed as supplements, and, further, functional nutritional foods. Also, the composition and agent according to the present invention can be blended in various foods to be provided.

When the composition and agent according to the present invention are provided as foods, the foods may be attached with an indication that the foods have the action of promoting ketone body production. In this case, in order that consumers can easily understand the indication, the foods of the present invention may be attached with an indication which suggests the alleviation, maintenance and improvement of diseases that are to be effectively treated, prevented or improved by promoting ketone body production and symptoms related to the diseases, for example, "maintaining/supporting the cognitive function."

When the composition and agent according to the present invention are provided as foods, the foods contain an effective amount of the amino acid of the present invention (or the amino acid of the present invention and either or both of a medium-chain fatty acid and a medium-chain fatty acid ester). Here, the phrase "containing an effective amount" of the amino acid of the present invention (or the amino acid of the present invention and either or both of a medium-chain fatty acid and a medium-chain fatty acid ester) refers to a content which allows feeding of the amino acid of the present invention (or the amino acid of the present invention and either or both of a medium-chain fatty acid and a medium-chain fatty acid ester) in an amount within a range as will be described later when individual foods are fed in a normally eaten amount. The term "food" used herein includes health foods, functional foods, functional health foods (such as designated health foods, functional nutritional foods, nutritional supplements and foods with function claims), foods for special dietary uses (such as foods for infants, foods for expectant and nursing mothers, foods for patients), and medical foods (foods formulated under the control of a doctor, defined by the U.S. Food and Drug Administration (FDA) and the Orphan Drug Act). The composition and agent according to the present invention comprise an ingredient which can be utilized as a food, and thus can be prepared as liquid foods, oral/tube feeding nutrients, beverages, gel foods (especially, so-called functional foods) or the like in expectation of promoting ketone body production and effects related thereto, and used in the nutritional management of patients who get nutrition orally/enterally, aged persons, babies and infants, etc.

The form of the "food" is not particularly limited, and may be a solid form such as a bar, a liquid form such as a beverage or a liquid food, a paste form, a semi-liquid form, a gel form, a powder form, or the like. Regardless of the form such as a solid form, a liquid form or a powder form, the composition and agent according to the present invention may be added to various foods (such as confectioneries such as chocolate and ice cream, cow milk, refreshing beverages, fermented milk, yogurt, cheese, bread, biscuit, cracker, pizza crust, modified milk powder, liquid foods, foods for special dietary uses, foods for patients, nutritional foods, frozen foods, processed foods, and other commercial foods), and the foods added therewith may be fed. When the nutritional composition is used in the form of a powder, the composition can be manufactured, for example, by spray-drying, freeze-drying or any other means.

When the composition and agent according to the present invention are provided as foods, the foods preferably comprise an ingredient which serves as a source of ketone body production in a living body (for example, either or both of a fatty acid and a fatty acid ester, preferably either or both of a medium-chain fatty acid and a medium-chain fatty acid ester) from the viewpoint of better exertion of the ketone body production promoting effect due to the amino acid of the present invention.

Examples of the food containing either or both of a medium-chain fatty acid and a medium-chain fatty acid ester include, but are not limited to, Ketonformula (manufactured by Meiji Co. Ltd.), Macton oil (manufactured by Kissei Pharmaceutical Co., Ltd.), MCT powder (manufactured by The Nissin Oillio Group, Ltd.), coconut oil and foods added with these foods.

The daily intake amount or dose of the composition and agent according to the present invention as foods or pharmaceutical products is not particularly limited as varying depending on the subject's pathological condition, age, symptom, body weight and use and whether they are only foods to be fed or pharmaceutical products to be administered for nutrition. In the case of feeding and administration for the purpose of promoting ketone body production in a living body and the action and effect related thereto, it is possible to feed or administer the composition and agent according to the present invention, for example, so that the amino acid of the present invention can be fed in an amount of 0.2 to 10 g, preferably 0.5 to 5 g, more preferably 1 to 3 g per day for an adult. The intake amount and dose can also be determined by a doctor in charge of the subject. When two or more amino acids of the present invention are blended in the composition and agent according to the present invention, the above effective intake amount and dose are the total amount of the two or more amino acids.

The composition and agent according to the present invention can be fed or administered together with a food, a food additive and a pharmaceutical product which effectively promote ketone body production. Examples of substances which can be fed or administered together include MCT oil and ketone esters such as 1,3-butandiol.

The composition and agent according to the present invention can be provided as a composition in a daily intake amount or dose which is effective for promoting ketone body production in a living body and the action and effect related thereto. In this case, the composition and agent according to the present invention may be packaged so as to allow feeding of an effective daily intake amount, and the package form may be composed of one package or a plurality of packages as long as the effective daily intake amount can be fed. When the composition and agent according to the present invention are provided in a package form, it is desirable that a description concerning the intake amount or dose be given on the package or that a document with the description be provided together with the package form, in order that the subject can easily recognize the effective daily intake amount or dose. When the effective daily intake amount or dose is provided in the form of a plurality of packages, it is also possible to provide, as a set, a plurality of packages containing the effective daily intake amount or dose for convenience of feeding or administration.

The package form for providing the composition and agent according to the present invention is not particularly limited as long as it is a form which defines a constant amount, including package papers, bags, soft bags, paper containers, cans, bottles, capsules, and other containers in which the composition and agent can be contained.

The composition and agent according to the present invention are preferably administered or fed continuously for one week or more to exert the effect better, and the period for administration and feeding is more preferably four weeks or more, particularly preferably about twelve weeks or more. Here, the term "continuously" means that feeding or administration is continued every day. When the composition and agent according to the present invention are provided in a package form, effective intake amounts or doses for a constant period (for example, four weeks) may be provided as a set for continuous feeding or administration.

EXAMPLES

Hereinafter, the present invention will be described in more detail by way of the following examples, but is not limited thereto.

Measurement of β-hydroxybutyric Acid Concentration

In the following Examples, the blood β-hydroxybutyric acid concentration was measured with a β-hydroxybutyric acid measuring instrument for self-inspection (Precision Xceed manufactured by Abbott).

Evaluation of Promotion of Ketone Body Production

Figure 1B:
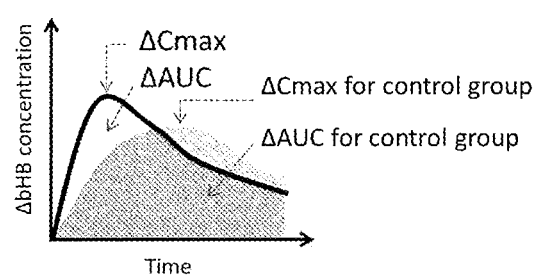
FIG. 1B is a reference view showing the maximum blood concentration (ΔCmax) and area under the blood concentration-curve (ΔAUC) of β-hydroxybutyric acid until the elapse of a predetermined time from an initial value (0 hours), when the concentration of β-hydroxybutyric acid originally present in the blood at the initial value (0 hours) before feeding of the test substance is assumed to be 0.
Figure 2:
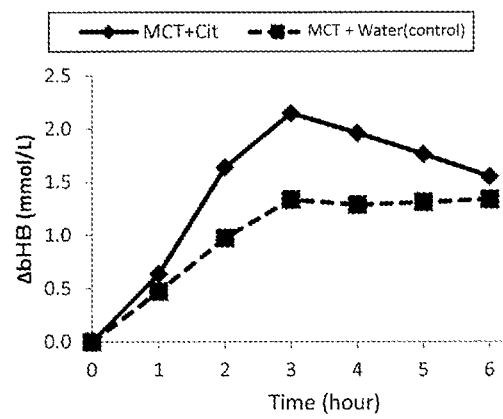
FIG. 2 is a graph showing the transition of the amount of change (ΔbHB) in concentration of β-hydroxybutyric acid (bHB) in the blood until 6 hours after simultaneous feeding of citrulline (Cit) and medium-chain fatty acid oil and fat (MCT) for an experimental group and a control group.

In the following Examples, the promotion of ketone body production was evaluated as follows. Specifically, blood was collected from the caudal vein of rats under fasting to measure the blood concentration (mmol/L) of β-hydroxybutyric acid (bHB) as an index of the ketone body in the blood. The measured value was defined as an initial value (0 hours). The rats were grouped into a control group and an experimental group, and fed with test samples. Thereafter, the transition of the blood bHB concentration until after 6 hours from the initial value was graphed. A reference view for determining the maximum blood concentration (Cmax) and area under the blood concentration-curve (AUC) of bHB is shown in FIG. 1A. A value obtained by subtracting the measured value at the initial value (0 hours) from the measured value at the time of each measurement was calculated, and defined as an amount of change in blood β-hydroxybutyric acid concentration (ΔbHB concentration) (FIG. 1B). Then, for the amount of change in blood β-hydroxybutyric acid concentration (ΔbHB concentration), the maximum blood concentration (ΔCmax) and area under the blood concentration-curve (ΔAUC) until after 6 hours from the initial value (0 hours) were calculated (FIG. 1B).

A % relative value (% ΔCmax (%)) of the maximum blood concentration ΔCmax of β-hydroxybutyric acid for the experimental group when the maximum blood concentration ΔCmax of β-hydroxybutyric acid for the control group was assumed to be 100 was determined according to the following calculation formula.

$$\% \, \Delta C\text{max}(\%) = \frac{\Delta C\text{max for test group}}{\Delta C\text{max for control group}} \times 100 \qquad [\text{Mathematical Formula 1}]$$

A % relative value (% ΔAUC (%)) of the area under the blood concentration-curve ΔAUC of blood β-hydroxybutyric acid for the experimental group when the area under the blood concentration-curve ΔAUC of blood β-hydroxybutyric acid for the control group was assumed to be 100 was determined according to the following calculation formula.

$$\% \, \Delta AUC(\%) = \frac{\Delta AUC \text{ for test group}}{\Delta AUC \text{ for control group}} \times 100 \qquad [\text{Mathematical Formula 2}]$$

Example 1

Selection of Amino Acid Promoting Ketone Body Production

Male Wistar rats (obtained from Japan SLC, Inc.) were acclimated for one week and then used for testing. Blood was collected from the caudal vein of the rats under overnight fasting to measure the blood concentration (mmol/L) of β-hydroxybutyric acid (bHB) as an index of the ketone body in the blood. The rats were grouped (n=8 for each group) so that the averages of the body weights and the β-hydroxybutyric acid concentrations for the respective groups were as equal as possible. Then, water was orally fed in an amount of 10 mL/kg of the body weight to the control group, and aqueous solutions of various amino acids (manufactured by Wako Pure Chemical Industries, Ltd.) were orally fed in an amount of 1.0 mmol/kg of the body weight to the experimental group. Immediately after feeding of water or each of the aqueous amino acid solutions, caprylic triglyceride (manufactured by Tokyo Chemical Industry Co., Ltd.), which is medium-chain fatty acid oil and fat (MCT), was orally fed in an amount of 3.0 g/kg of the body weight to the groups. Blood was collected from the caudal vein 1, 2, 3, 4, 5, and 6 hours after feeding of MCT to measure the blood β-hydroxybutyric acid concentration.

As a result of reviews on the various amino acids, six amino acids, i.e., citrulline (Cit), leucine (Leu), cysteine (Cys), taurine (Tau), glutamine (Gln) and aspartic acid (Asp), were selected as the amino acids by which both the % relative value (% ΔCmax (%)) of the maximum blood concentration ΔCmax of β-hydroxybutyric acid and the relative value (% ΔAUC (%)) of the area under the blood concentration-curve ΔAUC of β-hydroxybutyric acid for the experimental group were higher than those for the control group fed with water.

The measurement results concerning the six amino acids were as follows.

TABLE 1

Measurement results concerning six amino acids

|  | % ΔCmax (%) | % ΔAUC (%) |
|---|---|---|
| Citrulline (Cit) | 112.8 ± 25.5 | 105.4 ± 37.2 |
| Leucine (Leu) | 130.1 ± 31.8 | 110.5 ± 21.1 |
| Cysteine (Cys) | 151.9 ± 23.8 | 128.3 ± 22.2 |
| Taurine (Tau) | 137.8 ± 21.8 | 103.6 ± 23.0 |
| Glutamine (Gln) | 121.2 ± 44.6 | 103.6 ± 30.7 |
| Aspartic acids (Asp) | 108.8 ± 23.6 | 107.5 ± 30.7 |

Example 2

Effect of Citrulline or Leucine on Ketone Body Production in Feeding of Medium-Chain Fatty Acid Oil and Fat Male Wistar rats (obtained from Japan SLC, Inc.) were acclimated for one week and then used for testing. Blood was collected (0 hours) from the caudal vein of the rats under four-hour fasting to measure the β-hydroxybutyric acid (bHB) (mmol/L) in the blood as an index of the ketone body in the blood. The rats were grouped (three groups, i.e., the control group and the experimental groups; n=8 for each) so that the averages of the body weights and the β-hydroxybutyric acid concentrations for the respective groups were as equal as possible. Then, water was orally fed in an amount of 10 mL/kg of the body weight to the control group, and citrulline (Cit) or leucine (Leu) was orally fed in an amount of 1.5 mmol/kg of the body weight to the experimental groups. Immediately after feeding of water or the aqueous citrulline or leucine solution, caprylic triglyceride (manufactured by Tokyo Chemical Industry Co., Ltd.) as the medium-chain fatty acid oil and fat (MCT) was orally fed in an amount of 4.5 g/kg of the body weight to the groups. Blood was collected from the caudal vein 1, 2, 3, 4, 5, and 6 hours after feeding of MCT to measure the blood β-hydroxybutyric acid concentration.

The results were as shown in FIGS. 2 to 7. From the results shown in FIGS. 2 to 4, it was confirmed that, when citrulline (Cit) was fed together with the medium-chain fatty acid oil and fat (MCT), the ketone body production was promoted as compared with the case where the medium-chain fatty acid oil and fat (MCT) was fed alone. Also, from the results shown in FIGS. 5 to 7, it was confirmed that, when leucine (Leu) was fed together with the medium-chain fatty acid oil and fat, the ketone body production was promoted as compared with the case where the medium-chain fatty acid oil and fat (MCT) was fed alone.

Example 3

Effect of Citrulline Amount on Ketone Body Production in Feeding of Medium-Chain Fatty Acid Oil and Fat Male Wistar rats (obtained from Japan SLC, Inc.) were acclimated for one week and then used for testing. Blood was collected (0 hours) from the caudal vein of the rats under four-hour fasting to measure the blood β-hydroxybutyric acid concentration (mmol/L) as an index of the ketone body in the blood. The rats were grouped (two groups, i.e., the control group and the experimental group; n=10 for each) so that the averages of the body weights and the β-hydroxybutyric acid concentrations for the respective groups were as equal as possible. Then, water was orally fed in an amount of 10 ml/kg of the body weight to the control group, and an aqueous solution of citrulline was fed to the experimental group in an amount of 1.5 mmol/kg of the body weight, 2.25 mmol/kg of the body weight or 3.0 mmol/kg of the body weight, respectively. Immediately after feeding of water or the aqueous citrulline solution, caprylic triglyceride (manufactured by Riken Vitamin Co., Ltd.) as the medium-chain fatty acid oil and fat (MCT) was orally fed in an amount of 4.5 g/kg of the body weight to the groups. Blood was collected from the caudal vein 1, 2, 3, 4, 5, and 6 hours after feeding of MCT to measure the blood β-hydroxybutyric acid concentration. Similarly to Example 1, the maximum blood concentration (ΔCmax) and area under the blood concentration-curve (ΔAUC) of β-hydroxybutyric acid (bHB) until after 6 hours from the initial value (0 hours) were calculated, and the % relative value (% ΔCmax (%)) of the maximum blood concentration ΔCmax of β-hydroxybutyric acid and the relative value (% ΔAUC (%)) of the area under the blood concentration-curve ΔAUC of β-hydroxybutyric acid, for the experimental group, to those for the control group were obtained.

The results are shown in FIGS. 8 and 9. From the results shown in FIGS. 8 and 9, it was confirmed that, when MCT was fed in a constant amount, the amount of the ketone bodies produced varied according to the intake amount of citrulline (Cit), and that an optimum citrulline (Cit) dose for promoting ketone body production was present.

The invention claimed is:

1. A method for promoting ketone body production to treat, prevent, or improve a disease or symptom that can be treated, prevented or improved by promoting ketone body production in a subject in need thereof, comprising feeding or administering to the subject one or more amino acid(s) selected from the group consisting of citrulline, leucine, cysteine, taurine, glutamine and aspartic acid in an amount effective to treat, prevent, or improve the disease or symptom.

2. The method of claim 1, further comprising feeding or administering to the subject either or both of a medium-chain fatty acid and a medium-chain fatty acid ester in an amount effective to treat, prevent, or improve the disease or symptom.

3. The method of claim 1, wherein the amino acid is provided in a food product.

4. The method of claim 2, wherein the amino acid and either or both of the medium-chain fatty acid and medium-chain fatty acid ester are provided in a food product.

5. The method of claim 2, wherein the amino acid and the a medium-chain fatty acid and/or a medium-chain fatty acid ester are administered in a molar ratio [(A)/(B)] of the amino acid(s) (A) to the medium-chain fatty acid and/or medium-chain fatty acid ester (B) ranges from 0.1 to 0.5.

6. The method of claim 5, wherein the amino acid and either or both of the a medium-chain fatty acid and a medium-chain fatty acid ester are provided in a food product.

7. The method of claim 1, wherein the disease and symptom are one or more selected from the group consisting of childhood epilepsy, intractable epilepsy, glucose transporter 1 (GLUT1) deficiency, pyruvate dehydrogenase complex disorder, Alzheimer's disease, neurodegenerative disease, mild cognitive impairment, Parkinson's disease, traumatic brain injury, cancer, depression, autism, migraine, amyotrophic lateral sclerosis, narcolepsy, diabetes, heart failure, myocardial infarction, angina pectoris, and obesity.

* * * * *